(12) United States Patent
Miura et al.

(10) Patent No.: US 11,590,315 B2
(45) Date of Patent: Feb. 28, 2023

(54) INDWELLING CATHETER

(71) Applicant: TERUMO KABUSHIKI KAISHA, Tokyo (JP)

(72) Inventors: Manabu Miura, Hadano (JP); Yasunobu Zushi, Kai (JP); Shinya Kusunoki, Hakui (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 814 days.

(21) Appl. No.: 16/561,535

(22) Filed: Sep. 5, 2019

(65) Prior Publication Data
US 2019/0388593 A1 Dec. 26, 2019

Related U.S. Application Data

(63) Continuation of application No. PCT/JP2018/009073, filed on Mar. 8, 2018.

(30) Foreign Application Priority Data

Mar. 8, 2017 (JP) .............................. JP2017-044181
Sep. 29, 2017 (JP) .............................. JP2017-191304

(51) Int. Cl.
*A61M 25/00* (2006.01)
*A61L 29/14* (2006.01)
(Continued)

(52) U.S. Cl.
CPC ......... *A61M 25/0017* (2013.01); *A61L 29/06* (2013.01); *A61L 29/14* (2013.01); *C08G 18/00* (2013.01); *A61M 25/01* (2013.01)

(58) Field of Classification Search
CPC .... A61L 29/06; A61L 29/14; A61M 25/0017; A61M 25/01; A61M 2025/09133; C08L 75/04; C08G 18/00
See application file for complete search history.

(56) References Cited

U.S. PATENT DOCUMENTS 5,453,099 A   9/1995  Lee et al.
5,993,436 A  11/1999  Kitou et al.
(Continued)

FOREIGN PATENT DOCUMENTS

CN   1065597 A   10/1992
CN   1554687 A   12/2004
(Continued)

OTHER PUBLICATIONS

International Search Report (PCT/ISA/210) and translation and Written Opinion (PCT/ISA/237) dated May 29, 2018, by the Japanese Patent Office as the International Searching Authority for International Application No. PCT/JP2018/009073.
(Continued)

*Primary Examiner* — Tasnim Mehjabin Ahmed
(74) *Attorney, Agent, or Firm* — Buchanan Ingersoll & Rooney PC

(57) ABSTRACT

Provided is an indwelling catheter which is stiff when being inserted into a vessel such as a blood vessel, softens after indwelling in the vessel, and conforms to a shape in a direction in which the vessel runs. In the indwelling catheter, the maximum value of a catheter repulsive force in a dry state at 25° C. is 0.10 N or more; the maximum value of the catheter repulsive force when immersed in warm water at 37° C. is 0.01 to 0.25 N; a ratio of the maximum value of the catheter repulsive force in a dry state at 25° C. to the maximum value of the catheter repulsive force when immersed in warm water at 37° C. is in a range of 3.5:1 or more; and the maximum value of the catheter repulsive force when immersed in warm water at 37° C. is 0.027 N or less after 5 minutes from indwelling.

12 Claims, 3 Drawing Sheets

SETTING OF TEST SAMPLE

TEST CHART

(51) Int. Cl.
*A61M 25/01* (2006.01)
*A61L 29/06* (2006.01)
*C08G 18/00* (2006.01)

(56) References Cited

U.S. PATENT DOCUMENTS

| | | | |
|---|---|---|---|
| 6,193,699 | B1 | 2/2001 | Matsumoto et al. |
| 6,342,047 | B1 * | 1/2002 | Urakawa ............ C08G 18/4277 525/458 |
| 2007/0173927 | A1 | 7/2007 | Shin et al. |
| 2008/0119825 | A1 | 5/2008 | Imai et al. |
| 2012/0249662 | A1 | 10/2012 | Yamasaki et al. |
| 2013/0006222 | A1 | 1/2013 | Nabeshima et al. |
| 2017/0107320 | A1 * | 4/2017 | Zhou ....................... A61L 29/06 |

FOREIGN PATENT DOCUMENTS

| | | |
|---|---|---|
| CN | 101090744 A | 12/2007 |
| CN | 102732090 A | 10/2012 |
| CN | 102811759 A | 12/2012 |
| CN | 105983138 A | 10/2016 |
| EP | 0 962 227 A1 | 12/1999 |
| EP | 1 149 598 A2 | 10/2001 |
| JP | 04221571 A | 8/1992 |
| JP | 05084293 A | 4/1993 |
| JP | 2000051344 A | 2/2000 |
| JP | 2000051345 A | 2/2000 |
| JP | 2008104766 A | 5/2008 |
| JP | 4570707 B2 | 10/2010 |
| KR | 10-0664531 B1 | 1/2007 |

OTHER PUBLICATIONS

An English Translation of the International Search Report (Form PCT/ISA/210) and the Written Opinion of the International Searching Authority (Form PCT/ISA/237) dated May 29, 2018, by the Japanese Patent Office in corresponding International Application No. PCT/JP2018/009073. (13 pages).

Office Action (First Office Action) dated Jun. 29, 2021, by the State Intellectual Property Office of People's Republic of China in corresponding Chinese Patent Application No. 201880004603.5 and an English Translation of the Office Action. (18 pages).

Xiang et al., "Adhesive Foundation and Formula Design", Chemical Industry Press, 1st Edition, (Jan. 31, 2002), pp. 83-84. Discussed in Office Action (Second Office Action) dated Dec. 9, 2021, by the National Intellectual Property Administration in corresponding Chinese Patent Application No. 201880004603.5).

Office Action (Second Office Action) dated Dec. 9, 2021, by the National Intellectual Property Administration in corresponding Chinese Patent Application No. 201880004603.5 and an English Translation of the Office Action. (15 pages).

The extended European Search Report dated May 26, 2020, by the European Patent Office in corresponding European Patent Application No. 18763291.4-1109. (8 pages).

* cited by examiner

SETTING OF TEST SAMPLE

TEST CHART

CATHETER 2 (EXAMPLE 2)

CATHETER 12 (COMPARATIVE EXAMPLE 3)

SURFLOW (COMPARATIVE EXAMPLE 6)

CATHETER 2
(EXAMPLE 2)

CATHETER 12
(COMPARATIVE EXAMPLE 3)

SURFLOW
(COMPARATIVE EXAMPLE 6)

INDWELLING CATHETER

CROSS-REFERENCES TO RELATED APPLICATIONS

This application is a continuation of International Application No. PCT/JP2018/009073 filed on Mar. 8, 2018, and claims priority to Japanese Application No. 2017-044181 which was filed on Mar. 8, 2017, and Japanese Application No. 2017-191304 which was filed on Sep. 29, 2017, the entire contents of which are incorporated herein by reference.

TECHNICAL FIELD

The present disclosure relates to an indwelling catheter.

BACKGROUND DISCUSSION

An indwelling needle used for an infusion solution and blood transfusion or the like can be a plastic catheter capable of indwelling in a blood vessel. The indwelling needle to be used can be connected to a tube extending from a receptacle, such as an infusion solution bag, containing an infusion solution or a medicinal solution in a state where the indwelling needle is indwelled in the blood vessel. The indwelling needle can have an integral structure through which a sharp-tipped internal needle made of metal or the like extends. This type of indwelling needle can be punctured into the blood vessel together with the internal needle and the catheter, and the internal needle is then withdrawn from the indwelling needle, and used in the same manner as described above.

Since it can be beneficial to secure a flow path of the indwelled catheter in order to perform injection of an infusion solution and a medicinal solution, it can be beneficial for the catheter to have excellent kink resistance. Furthermore, since operability when punctured and interaction of a blood vessel wall when punctured and after indwelled are affected by the mechanical properties of the catheter, it can be desirable for the catheter to have sufficient stiffness when punctured, and soften after indwelled.

Fluoroplastics such as polytetrafluoroethylene, ethylenetetrafluoroethylene copolymers can be used (for example, mainly used) as the material of the indwelling catheter. Since catheters made of fluoroplastics are stiff and have stiffness when punctured, the catheters are excellent in operability, and are likely to secure a blood vessel. However, catheters made of fluoroplastics do not sufficiently soften after indwelled in the vessel, and may damage the blood vessel wall. They are insufficient in kink resistance, which may pose a problem for securing the flow path of the infusion solution.

In view of such circumstances, polyurethane resins, which contain hard segments and soft segments and in which the soft segments contain a polyether, have recently been used as catheter materials for indwelling needles. For example, JP 4570707 B discloses an indwelling catheter containing a blend of a plurality of polyurethane resins containing polyglycols having different molecular weights.

SUMMARY

JP 4570707 B discloses an indwelling catheter which is stiff when inserted into a blood vessel and softens after indwelled in a vessel.

The indwelling catheter described in JP 4570707 B softens after indwelled in the vessel, but the catheter cannot conform to a shape in a direction in which the vessel runs, and tries to return to the original linear shape of the catheter. It has been pointed out that, as the force trying to return to the original shape causes the tip of the catheter to continuously push the blood vessel wall, the inner wall tissue of the blood vessel may be damaged.

Therefore, exemplary aspects of the present disclosure have been made in view of the above circumstances, and it is an exemplary object of the present disclosure to provide an indwelling catheter which is stiff when being inserted into a vessel such as a blood vessel, softens after indwelled in the vessel, and conforms to a shape in a direction in which the vessel runs.

The inventors have conducted intensive studies to solve or ameliorate the above problems. A first exemplary embodiment of the present disclosure provides a indwelling catheter, wherein: a maximum value of a catheter repulsive force in a dry state at 25° C. is in a range of 0.10 N or more; a maximum value of the catheter repulsive force when immersed in warm water at 37° C. is in a range of 0.01 to 0.25 N; a ratio of the maximum value of the catheter repulsive force in a dry state at 25° C. to the maximum value of the catheter repulsive force when immersed in warm water at 37° C. is in a range of 3.5:1 or more; and the maximum value of the catheter repulsive force when immersed in warm water at 37° C. is in a range of 0.027 N or less after 5 minutes from indwelling.

A second exemplary embodiment of the present disclosure provides the indwelling catheter, wherein: the indwelling catheter contains a polyurethane resin; the polyurethane resin contains, for example, mainly contains, an aromatic diisocyanate, an aliphatic diol, and an aromatic polyglycol or an aliphatic polyglycol; a weight ratio of the diisocyanate to the polyglycol is in a range of 0.99:1 to 1.36:1; and the polyurethane resin contains a hard segment, wherein an average chain length of the hard segment is in a range of 1.00 to 3.01.

DETAILED DESCRIPTION

Figure 1:
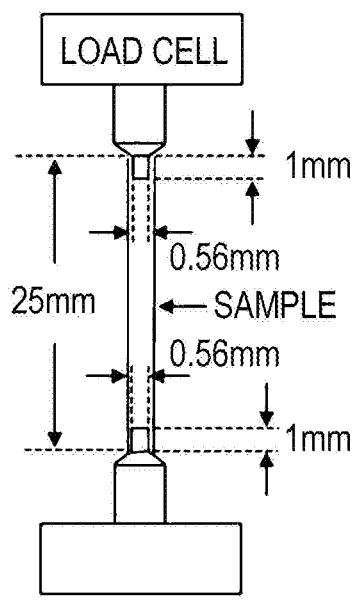
FIG. 1 shows a schematic view of setting of a test sample in pushability and kink distance measured in examples, and an example of a chart obtained in a test.
Figure 1:
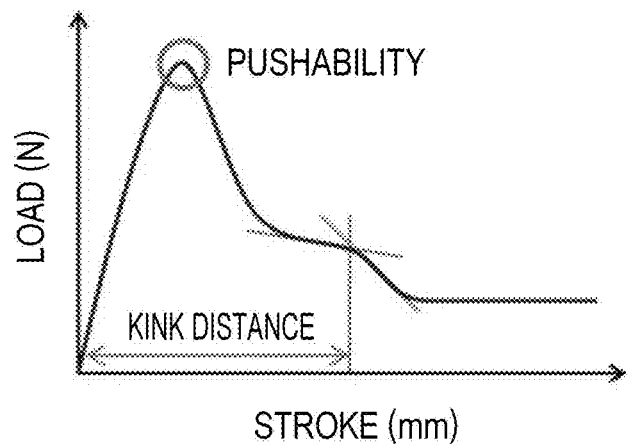

Hereinafter, an exemplary embodiment of the present disclosure will be described. The present disclosure is not limited to the following exemplary embodiment.

In the present specification, "X to Y" indicating a range means "X or more and Y or less". Unless otherwise specified, operations and measurements of physical properties or the like are measured under conditions of room temperature (25±1° C.)/relative humidity (40 to 50% RH).

First Exemplary Embodiment

A first exemplary embodiment of the present disclosure is an indwelling catheter, wherein: a maximum value of a catheter repulsive force in a dry state at 25° C. is 0.10 N or more; a maximum value of the catheter repulsive force when immersed in warm water at 37° C. is 0.01 to 0.25 N; a ratio of the maximum value of the catheter repulsive force in a dry state at 25° C. to the maximum value of the catheter repulsive force when immersed in warm water at 37° C. is in a range of 3.5:1 or more; and the maximum value of the catheter repulsive force when immersed in warm water at 37° C. is 0.027 N or less after 5 minutes from indwelling. The indwelling catheter according to the first exemplary embodiment of the present disclosure having such a configuration can be stiff when being inserted into a vessel such as a blood vessel, soften after indwelled in the vessel, and conform to a shape in a direction in which the vessel runs. As a result, the catheter can be easily advanced into the blood vessel. The catheter after indwelled in the vessel softens and has kink resistance, whereby the damage of the blood vessel (for example, caused by physical stimulation) can be reduced, and an administration route for a medicinal agent or the like can be secured. Furthermore, since the catheter after indwelling in the vessel conforms to a shape in a direction in which the vessel runs (that is, the tip of the catheter becomes parallel to the blood vessel), the damage of the blood vessel (for example, caused by physical stimulation) can be further reduced. In addition, the dosed medicinal agent can be inhibited from reaching the blood vessel wall in a high concentration, whereby chemical stimulation can also be reduced.

In the present specification, the maximum value of the catheter repulsive force is a value of a repulsive force obtained by subjecting a catheter having a tube length of 20 mm to a three-point bending test under conditions of a distance of 15 mm between support points, a pushing distance of 1.5 mm, and a pushing speed of 20 mm/min.

The maximum value of the catheter repulsive force in a dry state at 25° C. is a value of a repulsive force when the catheter is pushed by 1.5 mm in air in a dry state at 25° C. The maximum value of the catheter repulsive force when immersed in warm water at 37° C. is a value of a repulsive force when the catheter is pushed by 1.5 mm in warm water after immersed in warm water at 37° C. for 3 minutes. The maximum value of the catheter repulsive force after 5 minutes from indwelling when immersed in warm water at 37° C. is a value of a repulsive force when the catheter is immersed for 3 minutes in warm water at 37° C., and then pushed by 1.5 mm in warm water, followed by maintaining the pushing distance of 1.5 mm for 5 minutes without a change in the pushing distance. Autograph EZ-L, manufactured by Shimadzu Corporation, can be used to measure the catheter repulsive force.

In the indwelling catheter of the first exemplary embodiment, the maximum value of the catheter repulsive force in a dry state at 25° C. is 0.10 N or more. When the maximum value of the catheter repulsive force in a dry state at 25° C. is less than 0.10 N, the catheter has insufficient hardness when being inserted into a vessel such as a blood vessel, to cause difficult puncture, which can be undesirable. The upper limit of the maximum value of the catheter repulsive force in a dry state at 25° C. is not particularly limited, and is, for example, 0.80 N or less, for example, 0.70 N or less.

In the indwelling catheter of the first exemplary embodiment, the maximum value of the catheter repulsive force when immersed in warm water at 37° C. is 0.01 to 0.25 N. If the maximum value of the catheter repulsive force when immersed in warm water at 37° C. is less than 0.01 N, a catheter tube may be crushed by the pressure of a subcutaneous tissue while the catheter indwelled, which can be undesirable. If the maximum value of the catheter repulsive force when immersed in warm water at 37° C. is more than 0.25 N, the catheter does not sufficiently soften after indwelled in the blood vessel, which may cause the damage of the blood vessel, which can be undesirable. The maximum value of the catheter repulsive force when immersed in warm water at 37° C. can be 0.20 or less, for example, 0.10 or less, for example, 0.05 or less, for example, 0.03 or less.

In the indwelling catheter of the first exemplary embodiment, the ratio of the maximum value of the catheter repulsive force in a dry state at 25° C. to the maximum value of the catheter repulsive force when immersed in warm water at 37° C. is in a range of 3.5:1 or more. If the ratio of the maximum value of the catheter repulsive force in a dry state at 25° C. to the maximum value of the catheter repulsive force when immersed in warm water at 37° C. is less than 3.5:1, the catheter has no stiffness when punctured, which makes it difficult to push the catheter, or the catheter has a large repulsive force during indwelling, and may disadvantageously cause the damage of the blood vessel wall, which can be undesirable. The ratio of the maximum value of the catheter repulsive force in a dry state at 25° C. to the maximum value of the catheter repulsive force when immersed in warm water at 37° C. can be in a range of 5.0:1 or more, for example, 7.0:1 or more, for example, 8.0:1 or more, from the viewpoint of softening after indwelled in the vessel. The ratio of the maximum value of the catheter repulsive force in a dry state at 25° C. to the maximum value of the catheter repulsive force when immersed in warm water at 37° C. is not particularly limited, and can be in a range of, for example, 100:1 or less, for example, 50:1 or less, for example, 25:1 or less. For example, the ratio of the maximum value of the catheter repulsive force in a dry state at 25° C. to the maximum value of the catheter repulsive force when immersed in warm water at 37° C. can be in a range of from 3.5:1 to 100:1, for example, 5.0:1 to 50:1, for example, 7.0:1 to 25:1.

In the indwelling catheter of the first exemplary embodiment, the maximum value of the catheter repulsive force when immersed in warm water at 37° C. is 0.027 N or less after 5 minutes from indwelling. If the maximum value of the catheter repulsive force when immersed in warm water at 37° C. is more than 0.027 N after 5 minutes from indwelling, the catheter does not conform to a shape in a direction in which the vessel runs, so that physical stimulation may be applied to the blood vessel, or the blood vessel may be damaged, which can be undesirable. The maximum value of the catheter repulsive force after 5 minutes from indwelling when immersed in warm water at 37° C. can be 0.025 N or less, for example, 0.018 N, from the viewpoint that the catheter conform to a shape in a direction in which the vessel runs. The lower limit of the maximum value of the catheter repulsive force after 5 minutes from indwelling when immersed in warm water at 37° C. is not particularly limited.

In the first exemplary embodiment of the present disclosure, the maximum value of the catheter repulsive force can be controlled by the material used for the indwelling catheter, and the thickness of the catheter, or the like.

As the material of the indwelling catheter, it is exemplary to use a polyurethane resin having a structure in which hard segments and soft segments are alternately connected. By using the polyurethane resin, the hardness and softness of the indwelling catheter can be controlled.

As disclosed with respect to the indwelling catheter described in JP 4570707 B, by blending a plurality of polyurethane resins containing polyglycols having different molecular weights, both hardness when being inserted into a vessel such as a blood vessel and softness after indwelled in the vessel can be achieved, and kink resistance can be improved. However, the present inventors have found that the catheter of JP 4570707 B after being indwelled is insufficiently deformed in a direction in which the vessel runs by blending a plurality of polyurethane resins containing polyglycols having different molecular weights. Therefore, the present inventors focused on tan δ (coefficient of viscosity), and was considered to control the length of the average chain length of the hard segment to control a change in tan δ with temperature, whereby the indwelling catheter conforms to a direction in which the vessel runs after indwelled in the vessel (is deformed).

The tan δ represents conversion efficiency from elastic energy to thermal energy. As the tan δ is larger, the accumulated elastic energy can be converted to the thermal energy. In the catheter indwelling in the vessel, the catheter may come in contact with the blood vessel wall during indwelling. At that time, the elastic energy is stored in the catheter, and the stored elastic energy continues to compress the blood vessel wall. When the elastic energy is converted to the thermal energy, a force compressing the blood vessel wall is lost, and the catheter is taken along the blood vessel wall. This is caused by the property of creep characteristics.

In order to improve the creep characteristics, it can be beneficial to increase the tan δ. As described above, the following finding is obtained, in which the length of the average chain length of the hard segment is controlled, to adjust the tan δ so as to increase the tan δ in the vicinity of a body temperature, whereby the indwelling catheter maintains a shape along the vessel in the vicinity of the body temperature after indwelled in the vessel, to conform to a direction in which the vessel runs. Even if a material is deformed, the applied elastic energy is converted into heat, so that a force trying to return to the original shape is reduced, and the material tries to maintain its deformed shape. Furthermore, if the material is deformed into other shape, the elastic energy is converted into heat as described above, whereby the material is stabilized in the shape. Such a property has been found to be applied to a medical device inserted into or indwelling in a body such as a vessel to produce an unprecedented function of applying no load to a living tissue.

The mechanism described herein is estimated, and the present disclosure is not limited by the estimated mechanism described herein.

In the first exemplary embodiment of the present disclosure, from the viewpoint that the exemplary effects of the present disclosure can be further exhibited, it can be that: the indwelling catheter contains a polyurethane resin; the polyurethane resin contains, for example, mainly contains, a diisocyanate, a diol chain extending agent, and a polyglycol; a weight ratio of the diisocyanate to the polyglycol is in a range of 0.99:1 to 1.36:1; and the polyurethane resin contains a hard segment, and an average chain length of the hard segment is in a range of 1.00 to 3.01. For example, as long as the polyurethane resins contained in the indwelling catheter of the present disclosure satisfy the above, one type of the polyurethane resins may be contained, or two or more thereof may be blended.

Hereinafter, exemplary components of the polyurethane resin will be described.

The diisocyanate is a material contained in the hard segment. Examples of the diisocyanate, which may be used, include an aromatic diisocyanate (e.g., 4,4'-diphenylmethane diisocyanate, 2,4-toluene diisocyanate or the like), an aliphatic diisocyanate (e.g., hexamethylene diisocyanate or the like), and an alicyclic diisocyanate (e.g., isophorone diisocyanate or the like). The diisocyanate can be an aromatic diisocyanate, for example, 4,4'-diphenylmethane diisocyanate, from the viewpoint of moldability and mechanical properties.

The content of the diisocyanate can be appropriately adjusted so that the weight ratio of the content of the diisocyanate to the content of the following polyglycol is, for example, in a range of 0.99:1 to 1.36:1.

The diol chain extending agent is not particularly limited as long as it is a low molecular weight diol. The diol chain extending agent can be an aliphatic diol from the viewpoint of moldability and mechanical properties. Examples of the aliphatic diol include 1,4-butanediol, ethylene glycol, diethylene glycol, triethylene glycol, propylene glycol, and 1,6-hexanediol. Among them, the aliphatic diol can be 1,4-butanediol from the viewpoint that the above-mentioned exemplary effects can be further exhibited.

The content of the diol chain extending agent is, for example, in a range of 1 to 15% by weight based on the total amount (100% by weight) of the diisocyanate, diol chain extending agent and polyglycol.

The polyglycol is a material contained in a soft segment. The polyglycol is not particularly limited. The polyglycol can be an aromatic polyglycol or an aliphatic polyglycol from the viewpoint that safety and water resistance can be further obtained. Examples of the aromatic polyglycol include dimethyl glycol phthalate. Examples of the aliphatic polyglycol include polycaprolactone glycol, polytetramethylene glycol, polyadipate glycol, polyether glycol, and polycarbonate glycol. Among them, the aliphatic polyglycol can be polycaprolactone glycol or polytetramethylene glycol from the viewpoint that the above exemplary effects can be further exhibited. One or two or more of the polyglycols may be contained in the polyurethane resin.

The molecular weight of the polyglycol can be selected appropriately to obtain a desired average chain length of the hard segment. If the molecular weight of the polyglycol is too large, the reaction does not proceed uniformly, which causes deteriorated mechanical physical properties. If the molecular weight is too small, the moldability deteriorates. The molecular weight of the polyglycol can be 200 to 2000, for example, 200 to 1000, for example, 250 to 550.

The content of the polyglycol can be appropriately adjusted in order to obtain the desired weight ratio of the diisocyanate to the polyglycol. The content of the polyglycol can be, for example, 30 to 55% by weight, for example, 37 to 47% by weight, based on the total amount (100% by weight) of the diisocyanate, diol chain extending agent, and polyglycol.

From the above, in an exemplary embodiment, in the polyurethane resin contained in the indwelling catheter, the diisocyanate is an aromatic diisocyanate; the diol chain extending agent is an aliphatic diol; and the polyglycol is an aromatic polyglycol or an aliphatic polyglycol. In an exemplary embodiment, the aromatic diisocyanate is 4,4'-diphenylmethane diisocyanate; the aliphatic diol is 1,4-butanediol; and the aliphatic polyglycol is polycaprolactone glycol or polytetramethylene glycol.

Regarding the composition of the material contained in the indwelling catheter, for example, the types and molecular weights of the diisocyanate, diol chain extending agent, and polyglycol can be determined by dissolving the catheter in a solvent (DMSO-d6 solution) and performing $^1$H-NMR measurement and $^{13}$C-NMR measurement.

In the polyurethane resin according to the first exemplary embodiment, the weight ratio of the diisocyanate to the polyglycol can be in a range of 0.99:1 to 1.36:1. When the weight ratio of the diisocyanate to the polyglycol is 0.99:1 or more, hardness can be imparted to the indwelling catheter to assist with insertion into a vessel such as a blood vessel. When the weight ratio of the diisocyanate to the polyglycol is 1.36:1 or less, the catheter after indwelled in the vessel can soften.

In the indwelling catheter of the first exemplary embodiment, the polyurethane resin may be a blend of two or more polyurethane resins. When the two or more types of polyurethane resins are blended, an average value calculated from the blending weight ratio of the polyurethane resins to be blended is taken as a "weight ratio of a diisocyanate to a polyglycol". For example, when two polyurethane resins having weight ratios of a diisocyanate to a polyglycol of 0.99:1 and 1.28:1 are mixed and blended at a blending weight ratio of 75:25, the weight ratio of the diisocyanate to the polyglycol of the polyurethane resin is calculated to be 1.06:1 according to the formula: {(0.99×75)+(1.28×25)}/100.

In the polyurethane resin according to the first exemplary embodiment, the average chain length of the hard segment can be 1.00 to 3.01. The average chain length of the hard segment in this range allows the catheter after indwelled in the vessel to conform to a shape in a direction in which the vessel runs.

For example, on the assumption that the molar ratio of [OH]/[NCO] is 1:1 from the molecular weights and composition ratios of the polyglycol, diisocyanate, and diol chain extending agent contained in the polyurethane resin, the average chain length of the hard segment is a value calculated using the following formula (3). For example, when polycaprolactone glycol (PCL) as the polyglycol, 4,4'-diphenylmethane diisocyanate (MDI) as the diisocyanate, and 1,4-butanediol (BD) as the diol chain extending agent are used, the hard segment and the soft segment are represented as follows assuming that the number of repeating units of (MDI-BD) are n.

[Chemical Formula 1]

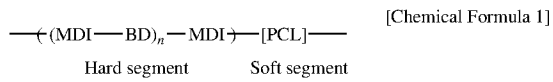

Hard segment    Soft segment

When the molar ratio of [OH]/[NCO] is 1:1, [OH] is [NCO], whereby the following formula (1) is represented assuming that the molecular weights of PCL, MDI, and BD are respectively $M_{PCL}$, $M_{MDI}$, and $M_{BD}$, and the weight fraction of the soft segment (PCL) is X.

[Expression 1]

$$\frac{X}{M_{PCL}} = \frac{1-X}{n(M_{MDI} + M_{BD}) + M_{MDI}} \qquad \text{Formula (1)}$$

When the above equation is solved for n, the following formula (2) is represented.

[Expression 2]

$$n = \frac{\left\{M_{PCL}\left(\frac{1-X}{X}\right) - M_{MDI}\right\}}{(M_{MDI} + M_{BD})} \qquad \text{Formula (2)}$$

Since the hard segment is (MDI-BD)$_n$-MDI as described above, the average chain length of the hard segment is n+1, which is calculated by the following formula (3).

[Expression 3]

Average chain length of hard segment = $\qquad$ Formula (3)

$$\frac{\left\{M_{PCL}\left(\frac{1-X}{X}\right) - M_{MDI}\right\}}{(M_{MDI} + M_{BD})} + 1$$

As is apparent from the formula (3), the minimum value of the average chain length of the hard segment is 1.00. The average chain length of the hard segment can be controlled by the molecular weights and composition ratios of the polyglycol, diisocyanate, and diol chain extending agent contained in the polyester resin.

As described above, the average chain length of the hard segment can be 3.01 or less. Since the average chain length of the hard segment can be 3.01 or less, each hard segment can exist as a finer segment. Therefore, for example, the catheter after indwelled in the vessel softens, and at the same time, the catheter can conform to a direction in which the vessel runs. The average chain length of the hard segment can be 2.30 or less, for example, 1.80 or less.

In the indwelling catheter of the first exemplary embodiment, the polyurethane resin may be a blend of two or more polyurethane resins. When the two or more types of polyurethane resins are blended, an average value calculated from the blending weight ratio of polyurethane resins to be blended is taken as an "average chain length of hard segment". For example, when two polyurethane resins having average chain lengths of hard segment f 1.59 and 1.28 are mixed and blended in a blending weight ratio of 75:25, the average chain length of the hard segment of the polyurethane resin is calculated to be 1.51 according to the formula of {(1.59×75)+(1.28×25)}/100.

The method for producing the polyurethane resin is not particularly limited, and the polyurethane resin can be produced by using any suitable method such as a one-shot method or a prepolymer method.

Second Exemplary Embodiment

A second exemplary embodiment of the present disclosure is an indwelling catheter containing a polyurethane resin, wherein: the polyurethane resin contains, for example, mainly contains, an aromatic diisocyanate, an aliphatic diol, and an aromatic polyglycol or an aliphatic polyglycol; a weight ratio of the diisocyanate to the polyglycol is in a range of 0.99:1 to 1.36:1; and the polyurethane resin contains a hard segment, and an average chain length of the hard segment is in a range of 1.00 to 3.01. The indwelling catheter according to the second exemplary embodiment of the present disclosure having such a configuration can be stiff when being inserted into a vessel such as a blood vessel, soften after indwelled in the vessel, and conform to a shape in a direction in which the vessel runs. As a result, the catheter can be easily advanced into the blood vessel. For example, the catheter after indwelled in the vessel softens and has kink resistance, whereby the damage of the blood vessel (for example, caused by physical stimulation) can be reduced, and an administration route for a medicinal agent or the like can be secured. Furthermore, since the catheter after indwelling in the vessel conforms to a shape in a direction in which the vessel runs (that is, the tip of the catheter becomes parallel to the blood vessel), the damage of the blood vessel (for example, caused by physical stimulation) can be further reduced. In addition, the dosed medicinal agent can be inhibited from reaching the blood vessel wall in a high concentration, whereby chemical stimulation can also be reduced.

The descriptions of the "polyurethane resin", "weight ratio of a diisocyanate to a polyglycol", and "average chain length of hard segment" in the present embodiment are the same as those in the first exemplary embodiment, and thus the descriptions thereof are omitted.

<<Method for Producing Indwelling Catheter>>

A method for producing the indwelling catheter of the present disclosure is not particularly limited, and any suitable method can be used. For example, a material (a polyurethane resin or the like) used for the indwelling catheter can be prepared by extrusion molding.

<<Application of Indwelling Catheter>>

The indwelling catheter of the present disclosure can be stiff when being inserted into a vessel such as a blood vessel, soften after indwelled in the vessel, and conform to a shape in a direction in which the vessel runs. Therefore, the indwelling catheter can be used in a state where the indwelling catheter is indwelled in the blood vessel for the purposes of injection of an infusion solution and medicinal solution into the body, blood transfusion, blood collection, and hemodynamic monitoring or the like.

EXAMPLES

Exemplary effects of the present disclosure will be described using the following Examples and Comparative Examples. However, the technical scope of the present disclosure is not limited to only the following Examples. The operation was performed at room temperature (25° C.) unless otherwise stated. Unless otherwise stated, "%" and "parts" mean "% by weight" and "parts by weight", respectively.

[Measurement of Maximum Value of Catheter Repulsive Force]

(Test Method)

A catheter having a length of 20 mm was subjected to a three-point bending test using Autograph (EZ-L, manufactured by Shimadzu Corporation) under conditions of a distance of 15 mm between support points, a pushing distance of 1.5 mm, and a pushing speed of 20 mm/min.

(Test Conditions)

The three-point bending test was performed under two conditions of a dry state at 25° C. and a warm water immersion state at 37° C.

In the test in a dry state at 25° C., a repulsive force when the catheter was pushed by 1.5 mm in air was measured.

The test in the warm water immersion state at 37° C. was started after 3 minutes from immersion in warm water, and a repulsive force when the catheter was pushed by 1.5 mm in warm water was measured, and a repulsive force after a pushing distance was maintained for 5 minutes without a change in the pushing distance after the catheter was pushed by 1.5 mm was measured.

[Calculation of Average Chain Length of Hard Segment]

In the examples, on the assumption that the molar ratio of [OH]/[NCO] is 1:1 from the molecular weights and composition ratios of the polyglycol, diisocyanate, and diol chain extending agent contained in the polyurethane resin, the average chain length of the herd segment is a value calculated using the following formula (3). For example, when polycaprolactone glycol (PCL) as the polyglycol, 4,4'-diphenylmethane diisocyanate (MDI) as the diisocyanate, and 1,4-butanediol (BD) as the diol chain extending agent are used, the hard segment and the soft segment are represented as follows assuming that the number of repeating units of MDI and BD are n.

[Chemical Formula 2]
$$-\!\!\!-\!\!(\text{MDI}-\text{BD})_n-\text{MDI}\!\!\:\!\!\!-\!\!\![\text{PCL}]-\!\!\!-$$
$$\underbrace{\phantom{(\text{MDI}-\text{BD})_n-\text{MDI}}}_{\text{Hard segment}} \quad \underbrace{\phantom{[\text{PCL}]}}_{\text{Soft segment}}$$

In the examples, when the molar ratio of [OH]/[NCO] is 1:1, [OH] is [NCO], whereby the following formula (1) is represented assuming that the molecular weights of PCL, MDI, and BD are respectively $M_{PCL}$, $M_{MDI}$, and $M_{BD}$, and the weight fraction of the soft segment (PCL) is X.

[Expression 4]
$$\frac{X}{M_{PCL}} = \frac{1-X}{n(M_{MDI}+M_{BD})+M_{MDI}} \quad \text{Formula (1)}$$

When the above formula is solved for n, the following formula (2) is represented.

[Expression 5]
$$n = \frac{\left\{M_{PCL}\left(\frac{1-X}{X}\right)-M_{MDI}\right\}}{(M_{MDI}+M_{BD})} \quad \text{Formula (2)}$$

Since the hard segment is $(\text{MDI-BD})_n\text{-MDI}$ as described above, the average chain length of the hard segment is n+1, which is calculated by the following formula (3).

[Expression 6]

Average chain length of hard segment = $\qquad$ Formula (3)
$$\frac{\left\{M_{PCL}\left(\frac{1-X}{X}\right)-M_{MDI}\right\}}{(M_{MDI}+M_{BD})}+1$$

In Examples, when two types of polyurethane resins were blended, as described above, an average value calculated from the blending weight ratios of the two types of polyurethane resins was taken as an average chain length of hard segment.

[Preparation of Polyurethane Resin]

Polycaprolactone glycol (PCL) or polytetramethylene glycol (PTMG) as a polyglycol, 4,4'-diphenylmethane diisocyanate (MDI) as a diisocyanate, and 1,4-butanediol (BD) as a diol chain extending agent were blended in a ratio described in Table 1 below, and polyurethane resins A to J were prepared by a one-shot method.

TABLE 1

| | Polyglycol | | | Diisocyanate | | | Diol-based chain extending agent | | | Weight ratio (diisocyanate/polyglycol) | Average chain length of hard segment |
|---|---|---|---|---|---|---|---|---|---|---|---|
| | Kind | Molecular weight | Weight composition (wt %) | Kind | Molecular weight | Weight composition (wt %) | Kind | Molecular weight | Weight composition (wt %) | | |
| Polyurethane resin A | PCL | 400 | 47.0 | MDI | 250 | 46.7 | BD | 90 | 6.3 | 0.99:1 | 1.59 |
| Polyurethane resin B | PTMG | 250 | 42.0 | MDI | 250 | 53.8 | BD | 90 | 4.2 | 1.28:1 | 1.28 |
| Polyurethane resin C | PCL | 400 | 42.0 | MDI | 250 | 49.6 | BD | 90 | 8.4 | 1.18:1 | 1.89 |
| Polyurethane resin D | PCL | 550 | 37.0 | MDI | 250 | 50.8 | BD | 90 | 12.2 | 1.37:1 | 3.02 |
| Polyurethane resin E | PCL | 550 | 42.0 | MDI | 250 | 47.7 | BD | 90 | 10.3 | 1.14:1 | 2.50 |
| Polyurethane resin F | PTMG | 250 | 37.0 | MDI | 250 | 56.1 | BD | 90 | 6.9 | 1.52:1 | 1.52 |
| Polyurethane resin G | PCL | 400 | 37.0 | MDI | 250 | 52.4 | BD | 90 | 10.6 | 1.42:1 | 2.27 |
| Polyurethane resin H | PCL | 2000 | 37.0 | MDI | 250 | 47.5 | BD | 90 | 15.5 | 1.29:1 | 10.28 |
| Polyurethane resin I | PTMG | 750 | 40.0 | MDI | 250 | 47.6 | BD | 90 | 12.4 | 1.19:1 | 3.57 |
| Polyurethane resin J | PTMG | 720 | 42.0 | MDI | 250 | 46.5 | BD | 90 | 11.5 | 1.11:1 | 3.19 |

PCL: Polycaprolactone glycol
PTMG: Polytetramethylene glycol
MDI: 4,4'-diphenylmethane diisocyanate
BD: 1,4-butanediol Example 1

A polyurethane resin A was subjected to extrusion molding to obtain an extrusion-molded product having an inner diameter of 0.64 mm and an outer diameter of 0.86 mm, and the extrusion-molded product was then subjected to an annealing treatment at 80° C. for 4 hours to prepare a catheter 1.

Example 2

A catheter 2 was prepared in the same manner as in Example 1 except that a polyurethane resin B was used instead of a polyurethane resin A.

Example 3

A catheter 3 was prepared in the same manner as in Example 1 except that a resin obtained by melt-blending a polyurethane resin A and a polyurethane resin B at a weight ratio of 75:25 was used instead of the polyurethane resin A.

Example 4

A catheter 4 was prepared in the same manner as in Example 1 except that a resin obtained by melt-blending a polyurethane resin C and a polyurethane resin B at a weight ratio of 67:33 was used instead of a polyurethane resin A.

Example 5

A catheter 5 was prepared in the same manner as in Example 1 except that a resin obtained by melt-blending a polyurethane resin C and a polyurethane resin A at a weight ratio of 60:40 was used instead of the polyurethane resin A.

Example 6

A catheter 6 was prepared in the same manner as in Example 1 except that a resin obtained by melt-blending a polyurethane resin D and a polyurethane resin C at a weight ratio of 25:75 was used instead of a polyurethane resin A.

Example 7

A catheter 7 was prepared in the same manner as in Example 1 except that a polyurethane resin C was used instead of a polyurethane resin A.

Example 8

A catheter 8 was prepared in the same manner as in Example 1 except that a resin obtained by melt-blending a polyurethane resin E and a polyurethane resin A at a weight ratio of 40:60 was used instead of the polyurethane resin A.

Example 9

A catheter 9 was prepared in the same manner as in Example 1 except that a polyurethane resin E was used instead of a polyurethane resin A.

Comparative Example 1

A catheter 10 was prepared in the same manner as in Example 1 except that a polyurethane resin F was used instead of a polyurethane resin A.

Comparative Example 2

A catheter 11 was prepared in the same manner as in Example 1 except that a polyurethane resin G was used instead of a polyurethane resin A.

Comparative Example 3

A catheter 12 was prepared in the same manner as in Example 1 except that a polyurethane resin H was used instead of a polyurethane resin A.

Comparative Example 4

A catheter 13 was prepared in the same manner as in Example 1 except that a polyurethane resin I was used instead of a polyurethane resin A.

Comparative Example 5

A catheter 14 was prepared in the same manner as in Example 1 except that a polyurethane resin J was used instead of a polyurethane resin A.

The maximum value of a catheter repulsive force in each condition for the catheters 1 to 14 prepared above and a catheter (Comparative Example 6; made of ETFE) of a commercially available indwelling needle (Surflow (registered trademark) (SR-OT2232C), Terumo Corporation) was measured, and a weight ratio of a diisocyanate to a polyglycol and an average chain length of hard segment were calculated. In Examples, when two types of polyurethane resins were blended, as described above, an average value calculated from the blending weight ratio of the two types of polyurethane resins was taken as the weight ratio of a diisocyanate to a polyglycol.

The results are shown in Table 2.

[Evaluation: Measurement of Pushability and Kink Distance]

The pushability and kink distance of each of the catheters 1 to 14 and the catheter of the commercially available indwelling needle (Surflow (registered trademark) SR-OT2232C, Terumo Corporation) prepared above were measured according to the following method. The results are shown in Table 3.

(Test Method)

The catheter was cut to a length of 25 mm to prepare a test sample, and the catheter was fixed by a jig having a diameter of 0.56 mm and a length of 1 mm. Using Autograph (EZ-L, manufactured by Shimadzu Corporation), the test sample was pushed at a pushing speed of 50 mm/min in air. The test sample was pushed until the test sample was kinked, or was pushed to 20 mm, to measure the pushability and the kink distance.

FIG. 1 shows a schematic view of the setting of the test sample and an example of a chart obtained in the test. The test sample is set as shown in FIG. 1, and the test sample is pushed from above and below to measure the pushability and the kink distance. As shown in the example of the chart of FIG. 1, when the test sample is pushed from above and below, the test sample is not deformed, and a load increases. However, as the pushing proceeds, the test sample begins to flex, to cause the load to decrease. In this test, a value before the load decreases, that is, when the load is maximized, is taken as "pushability". As further pushing proceeds, an inner cavity of the test sample collapses to cause the occlusion (i.e., kink) to begin, resulting in a greater change in load decrease to cause an inflection point in the chart. On the chart, the moving distance of a load cell determined and moved from a time point when the test is started (starting point) until the inflection point is generated in the chart is taken as a "kink distance".

TABLE 2

| | | Catheter repulsion force | | | | Polyurethane resin | |
| --- | --- | --- | --- | --- | --- | --- | --- |
| | Catheter number | 25° C. (dry state) (unit: N) | 37° C. (when immersed in warm water) (unit: N) | 25° C. (dry state)/37° C. (when immersed in warm water) | 37° C. (when immersed in warm water: after 5 minutes from indwelling) (unit: N) | Weight ratio (diisocyanate/ polyglycol) | Average chain length of hard segment |
| Example 1 | Catheter 1 | 0.193 | 0.018 | 10.6 | 0.011 | 0.99:1 | 1.59 |
| Example 2 | Catheter 2 | 0.697 | 0.029 | 24.0 | 0.003 | 1.28:1 | 1.28 |
| Example 3 | Catheter 3 | 0.202 | 0.010 | 20.4 | 0.006 | 1.06:1 | 1.51 |
| Example 4 | Catheter 4 | 0.380 | 0.018 | 21.1 | 0.008 | 1.21:1 | 1.69 |
| Example 5 | Catheter 5 | 0.227 | 0.023 | 10.0 | 0.013 | 1.10:1 | 1.77 |
| Example 6 | Catheter 6 | 0.390 | 0.039 | 9.9 | 0.019 | 1.23:1 | 2.17 |
| Example 7 | Catheter 7 | 0.536 | 0.042 | 12.6 | 0.019 | 1.18:1 | 1.89 |
| Example 8 | Catheter 8 | 0.115 | 0.018 | 6.5 | 0.011 | 1.05:1 | 1.95 |
| Example 9 | Catheter 9 | 0.112 | 0.028 | 3.9 | 0.017 | 1.14:1 | 2.50 |
| Comparative Example 1 | Catheter 10 | 0.852 | 0.519 | 1.6 | 0.047 | 1.52:1 | 1.52 |
| Comparative Example 2 | Catheter 11 | 0.834 | 0.288 | 2.9 | 0.047 | 1.42:1 | 2.27 |
| Comparative Example 3 | Catheter 12 | 0.132 | 0.068 | 2.3 | 0.031 | 1.29:1 | 10.28 |
| Comparative Example 4 | Catheter 13 | 0.143 | 0.070 | 2.0 | 0.043 | 1.19:1 | 3.57 |
| Comparative Example 5 | Catheter 14 | 0.297 | 0.106 | 2.8 | 0.043 | 1.11:1 | 3.19 |
| Comparative Example 6 | Surflow (ETFE) | 0.336 | 0.293 | 1.1 | 0.185 | — | — |

Herein, those which meet all the following criteria were accepted.

Pushability
dry state at 25° C.: 0.25 N or more
when immersed in warm water at 37° C.: 0.80 N or less
ratio of dry state at 25° C./when immersed in warm water at 37° C.: 2.00:1 or more Kink Distance
when immersed in warm water at 37° C.: 10 mm or more (Test Conditions)

Measurement was performed under two conditions of a dry state at 25° C. and after 3 minutes from a time point when immersed in warm water at 37° C. In the test after 3 minutes from the time point when immersed in warm water at 37° C., the measurement was started within 10 seconds after the immersed catheter was removed from the warm water.

[Evaluation: Conforming to Direction in which Vessel Runs]

Figure 2:
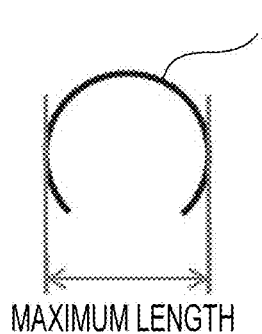
FIG. 2 shows a method for measuring a maximum length in conforming to a direction in which a vessel runs as measured in examples.
Figure 2:
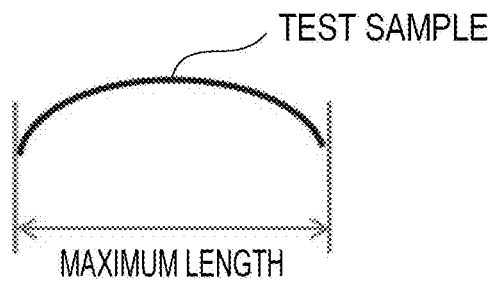

The catheter was cut into a length of 25 mm to prepare a test sample, and the test sample was wound around a cylinder having a diameter of 8 mm, and immersed in warm water at 37° C. for 3 minutes. The catheter was removed from the warm water, and the maximum length of the catheter (conforming to a direction in which a vessel runs) was measured after 10 seconds. The maximum length is the maximum width of the wound test sample, as shown in FIG. 2. Herein, the maximum length of 22 mm or less was accepted.

Since the catheter of Comparative Example 6 was broken during measurement, the catheter is not the object of the evaluation, but a measured value is shown in a parenthesis.

in warm water at 37° C.: 0.8 N or less; the ratio of pushability in a dry state at 25° C. to pushability when immersed in warm water at 37° C.: 2:1 or more).

(c) The catheter after indwelled in the vessel (when immersed in warm water at 37° C.) has kink resistance, and can secure an administration route (kink distance: 12 mm or more).

(d) Since the catheter conforms to a shape in a direction in which the vessel runs, the physical stimulation to the blood vessel and the damage of the blood vessel can be reduced (conforming to a direction in which the vessel runs (maximum length): 22 mm or less).

(e) Since the catheter conform to the shape in the direction in which the vessel runs, the tip of the catheter can be set to be parallel to the blood vessel, and the dosed medicinal agent is not applied to a blood vessel wall at a high concentration, whereby chemical stimulation can be reduced (conforming to a direction in which the vessel runs (maximum length): 22 mm or less).

It is found that, since the catheters of Examples 1 to 5 in which the average chain length of hard segment of the used polyurethane resin is in a range of 1.00 to 1.80, the catheters of Examples 1 to 5 have a more excellent balance between pushability (0.6 N or less) and a kink distance (13 mm or more) when immersed in warm water at 37° C. than those of Examples 6 to 9. Therefore, it is found that the catheters of Examples 1 to 5 further exhibit the exemplary effects of the above (b) and (c).

Meanwhile, it is found that at least one of the exemplary effects (a) to (e) cannot be obtained in the catheters of Comparative Examples.

TABLE 3

| | | Pushability | | | Kink distance (at 37° C.: when immersed in warm water) (unit: mm) | Conforming to direction in which vessel runs (unit: mm) |
|---|---|---|---|---|---|---|
| | Catheter number | 25° C. (dry state) (unit: N) | 37° C. (when immersed in warm water) (unit: N) | Ratio of 25° C. (dry state)/37° C. (when immersed in warm water) | | |
| Example 1 | Catheter 1 | 0.66 | 0.21 | 3.10:1 | 17.7 | 22 |
| Example 2 | Catheter 2 | 1.91 | 0.43 | 4.38:1 | 13.2 | 13 |
| Example 3 | Catheter 3 | 0.93 | 0.26 | 3.57:1 | 14.8 | 21 |
| Example 4 | Catheter 4 | 1.46 | 0.51 | 2.86:1 | 14.2 | 15 |
| Example 5 | Catheter 5 | 1.13 | 0.38 | 2.97:1 | 14.2 | 22 |
| Example 6 | Catheter 6 | 1.34 | 0.65 | 2.06:1 | 14.2 | 18 |
| Example 7 | Catheter 7 | 1.38 | 0.65 | 2.11:1 | 16.1 | 17 |
| Example 8 | Catheter 8 | 0.76 | 0.26 | 2.92:1 | 12.8 | 22 |
| Example 9 | Catheter 9 | 0.39 | 0.19 | 2.06:1 | 12.9 | 21 |
| Comparative Example 1 | Catheter 10 | 2.19 | 1.79 | 1.22:1 | 4.9 | 13 |
| Comparative Example 2 | Catheter 11 | 2.38 | 1.21 | 1.95:1 | 7.4 | 13 |
| Comparative Example 3 | Catheter 12 | 0.37 | 0.17 | 2.11:1 | 12.3 | 24 |
| Comparative Example 4 | Catheter 13 | 0.51 | 0.21 | 2.42:1 | 9.4 | 24 |
| Comparative Example 5 | Catheter 14 | 1.57 | 1.15 | 1.36:1 | 10.7 | 25 |
| Comparative Example 6 | Surflow (ETFE) | 0.97 | 0.85 | 1.14:1 | 5.4 | (17) |

As shown in Table 3, it is found that the catheters of Examples 1 to 9 have the following exemplary effects.

(a) When the catheter is inserted into a vessel such as a blood vessel (in a dry state at 25° C.), the catheter has sufficient pushability (0.25 N or more), whereby the catheter can be easily advanced into the blood vessel.

(b) The catheter after indwelled in the vessel (when immersed in warm water at 37° C.) softens, and can reduce the damage of the blood vessel (pushability when immersed It is found that the catheters of Comparative Examples 1, 2, 5 and 6 have large pushability values (more than 0.80 N) when immersed in warm water at 37° C., whereby the softness of the catheter after indwelled in the vessel is not sufficient.

The catheters of Comparative Examples 1, 2, 4, and 6 are found to have insufficient kink resistance (kink distance: less than 12 mm).

It is found that the catheters of Comparative Examples 3 to 5 insufficiently conform to a direction in which the vessel runs (conforming to a direction in which the vessel runs (maximum length): more than 22 mm).

It is found that, since the catheter of Comparative Example 6 is broken when the conforming to a direction in which the vessel runs is evaluated, and the conforming to a direction in which the vessel runs is not sufficient.

[Evaluation of Indwelling Shape and Pathological Observation]

Regarding the catheters 2 and 12 prepared above and the catheter of the commercially available indwelling needle (Surflow (registered trademark) SR-OT2232C, Terumo Corporation), the evaluation of the indwelling shape and the pathological observation were performed according to the following method.

(Test Method)

An indwelling needle for physical property evaluation (24G×¾") was inserted into each of rabbit left and right auricular veins at a puncture angle of 30°, indwelled, and was fixed. After the indwelling needle was filled with physiological saline, the indwelling needle was left for 24 hours to carry out the following evaluation.

1) Indwelling Shape

After indwelled for 24 hours, iohexol injection water (Omnipaque 140: Daiichi Sankyo Co., Ltd.) was injected into the indwelling needle for contrasting, to take an X-ray fluoroscopic image using an X-ray circulatory diagnosis system (Infinix-Celeve-i, manufactured by Toshiba Medical Systems). About the obtained X-ray fluoroscopic image, a line (represented by a broken line in FIG. 3) is drawn along the blood vessel from the tip of the catheter, and an angle between the line and the catheter (an angle between the catheter and the blood vessel back wall) (represented by a dashed line in FIG. 3) was measured. The results are shown in Table 4 and FIG. 3.

2) Pathological Observation

After indwelled for 24 hours, a vascular smooth muscle tissue around the tip of the catheter was collected, and fixed with formalin. Thereafter, a pathological specimen was prepared according to a standard method, subjected to hematoxylin-eosin staining (H & E staining), and observed with a light microscope. Furthermore, a slide in which the degeneration of the blood vessel was confirmed from the tissue specimen was subjected to immunostaining using an anti-α-SAM antibody as a smooth muscle marker of the blood vessel wall to confirm the impaired state of the blood vessel. The results are shown in Table 4 and FIG. 4.

TABLE 4

|  | Catheter 2 (Example 2) | Catheter 12 (Comparative Example 3) | Surflow (Comparative Example 6) |
|---|---|---|---|
| 1) Indwelling shape | 0° | 3° | 8° |
| 2) Pathology observation | No defects | Partial defects | Defects over entire circumference |

Figure 3:
FIG. 3 is an X-ray fluoroscopic image for evaluating an indwelling shape in examples. The two X-ray fluoroscopic images of examples or comparative examples are substantially identical, and in the lower X-ray fluoroscopic images, lines are drawn to indicate an angle between a catheter and a blood vessel back wall, according to an exemplary aspect.
Figure 3:
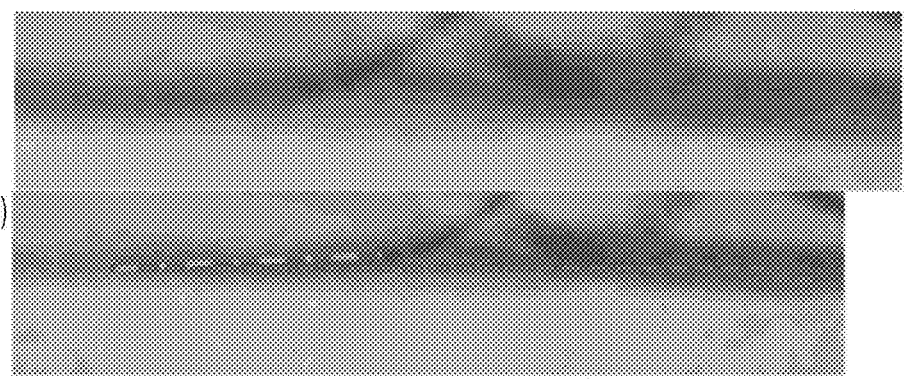
Figure 3:

As shown in Table 4 and FIG. 3, it is found that the catheter of Example 2 (Catheter 2) has an angle of 0° between the catheter and the blood vessel back wall, and conforms to a shape in a direction in which the vessel runs. Meanwhile, it is found that the catheters of Comparative Example 3 (Catheter 12) and Comparative Example 6 (Surflow) have an angle between the catheter and the blood vessel back wall larger than the 0° angle of Example 2, and insufficiently conform to a direction in which the vessel runs.

Figure 4:
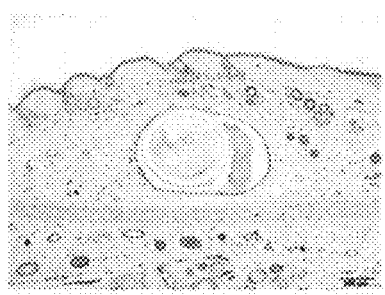
FIG. 4 is an optical micrograph of a vascular smooth muscle tissue for pathological observation in examples.
Figure 4:
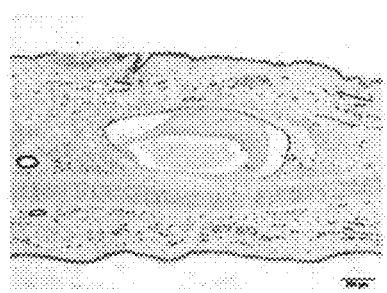
Figure 4:
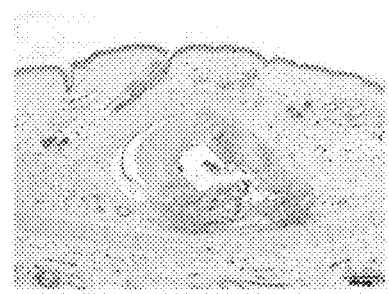

As shown in Table 4 and FIG. 4, it is found that, since the catheter of Example 2 (Catheter 2) conforms to a shape in a direction in which the vessel runs, there are no defects in vascular smooth muscle cells around the tip of the catheter. Meanwhile, it is found that, since the catheters of Comparative Example 3 (Catheter 12) and Comparative Example 6 (Surflow) insufficiently conform to a shape in a direction in which the vessel runs, there are defects in a part of the vascular smooth muscle tissue or over the entire circumference thereof.

This application is based on Japanese Patent Application No. 2017-044181 filed on Mar. 8, 2017 and Japanese Patent Application No. 2017-191304 filed on Sep. 29, 2017, the entire contents of which are incorporated herein by reference.

What is claimed is:

1. An indwelling catheter, wherein:
   a maximum value of a catheter repulsive force in a dry state at 25° C. is in a range of 0.10 N or more;
   a maximum value of a catheter repulsive force when immersed in warm water at 37° C. is in a range of 0.01 to 0.03 N;
   a ratio of the maximum value of the catheter repulsive force in the dry state at 25° C. to the maximum value of the catheter repulsive force when immersed in warm water at 37° C. is in a range of 7:1 or more; and
   the maximum value of the catheter repulsive force when immersed in warm water at 37° C. is in a range of 0.018 N or less after 5 minutes from indwelling;
   wherein the indwelling catheter contains a polyurethane resin;
   the polyurethane resin contains a diisocyanate, a diol chain extending agent, and a polyglycol;
   a weight ratio of the diisocyanate to the polyglycol is in a range of 0.99:1 to 1.36:1; and
   the polyurethane resin contains a hard segment, wherein an average chain length of the hard segment is in a range of 1.00 to 1.80.

2. The indwelling catheter according to claim 1, wherein:
   the diisocyanate is an aromatic diisocyanate;
   the diol chain extending agent is an aliphatic diol; and
   the polyglycol is an aromatic polyglycol or an aliphatic polyglycol.

3. The indwelling catheter according to claim 2, wherein:
   the aromatic diisocyanate is 4,4'-diphenylmethane diisocyanate;
   the aliphatic diol is 1,4-butanediol; and
   the aliphatic polyglycol is polycaprolactone glycol or polytetramethylene glycol.

4. The indwelling catheter according to claim 1, wherein the polyurethane resin contains a soft segment.

5. The indwelling catheter according to claim 4, wherein the polyurethane resin has a structure in which hard segments and soft segments are alternately connected.

6. The indwelling catheter according to claim 1, comprising
   a polyurethane resin, wherein:
   the polyurethane resin comprises (1) an aromatic diisocyanate, (2) an aliphatic diol, and (3) an aromatic polyglycol or an aliphatic polyglycol;
   a weight ratio of the aromatic diisocyanate to the aromatic polyglycol or the aliphatic polyglycol is in a range of 0.99:1 to 1.36:1.

7. The indwelling catheter according to claim 1, wherein the diol chain extending agent includes 1,4-butanediol, ethylene glycol, diethylene glycol, triethylene glycol, propylene glycol, or 1,6-hexanediol.

8. A method of using the indwelling catheter of claim 1, comprising:

inserting the indwelling catheter into a blood vessel, allowing the indwelling catheter to soften after indwelling in the blood vessel, and conforming the indwelling catheter to a shape in a direction in which the blood vessel runs.

9. An indwelling catheter, comprising a polyurethane resin, wherein:

the polyurethane resin comprises (1) an aromatic diisocyanate, (2) an aliphatic diol, and (3) an aromatic polyglycol or an aliphatic polyglycol;

a weight ratio of the aromatic diisocyanate to the aromatic polyglycol or the aliphatic polyglycol is in a range of 0.99:1 to 1.36:1; and the polyurethane resin contains a hard segment, wherein an average chain length of the hard segment is in a range of 1.00 to 1.80.

10. The indwelling catheter according to claim 9, wherein the polyurethane resin contains a soft segment.

11. The indwelling catheter according to claim 10, wherein the polyurethane resin has a structure in which hard segments and soft segments are alternately connected.

12. A method of using the indwelling catheter of claim 9, comprising:

inserting the indwelling catheter into a blood vessel, allowing the indwelling catheter to soften after indwelling in the blood vessel, and conforming the indwelling catheter to a shape in a direction in which the blood vessel runs.

* * * * *